United States Patent [19]

Kerschensteiner

[11] Patent Number: 4,623,629

[45] Date of Patent: Nov. 18, 1986

[54] SOLID-PHASE IMMUNOASSAY SUPPORT AND METHOD OF USE THEREOF

[76] Inventor: Daniel Kerschensteiner, 76 Q Farm Rd., Hillsborough, N.J. 08876

[21] Appl. No.: 546,799

[22] Filed: Oct. 31, 1983

[51] Int. Cl.$^4$ .......................................... G01N 33/543
[52] U.S. Cl. ..................... 436/518; 436/528; 436/529; 436/530; 436/532; 436/810; 435/7; 435/176; 435/177; 435/181
[58] Field of Search ............... 436/528, 529, 530, 532, 436/810, 826, 807, 518, 174, 176, 177; 435/7, 179, 181, 296

[56] References Cited

U.S. PATENT DOCUMENTS

| | | | |
|---|---|---|---|
| 3,790,663 | 2/1974 | Garrison et al. | 436/528 |
| 3,793,445 | 2/1974 | Updike et al. | 424/12 |
| 3,826,619 | 7/1974 | Bratu, Jr. et al. | 23/253 R |
| 3,951,748 | 4/1976 | Devlin | 195/103.5 R |
| 4,066,512 | 1/1978 | Lai et al. | 195/127 |
| 4,147,752 | 4/1979 | Suovaniemi et al. | 422/57 |
| 4,170,454 | 10/1979 | Meriadec et al. | 23/230.6 |
| 4,180,383 | 12/1979 | Johnson | 422/69 |
| 4,210,418 | 7/1980 | Brown et al. | 23/230 B |
| 4,225,784 | 9/1980 | Barrett | 250/303 |
| 4,280,816 | 7/1981 | Elahi | 23/230 B |
| 4,378,344 | 3/1983 | Zahradnik et al. | 436/500 |
| 4,397,959 | 8/1983 | Hechemy | 436/826 |
| 4,416,813 | 11/1983 | Ikeda et al. | 436/528 |

Primary Examiner—Christine M. Nucker
Assistant Examiner—Stephen C. Wieder
Attorney, Agent, or Firm—David A. Jackson

[57] ABSTRACT

A solid-phase immunoassay support is provided by treating a test tube liner such as a preformed soft gelatin capsule half with a coupling solution comprising a fixative, a bifunctional coupling agent and a bioactive protein which selectively reacts with the substance which is the subject of the immunoassay. The support is particularly applicable to the radioimmunoassay (RIA) technique for determining the presence and concentration of minute amounts of protein antigens in biological fluid samples and can be readily inserted in an appropriately sized test-tube for easy and quick assays.

21 Claims, No Drawings

SOLID-PHASE IMMUNOASSAY SUPPORT AND METHOD OF USE THEREOF

BACKGROUND OF THE INVENTION

1. Field of the Invention

This invention relates to an improved support for use in solid-phase immunoassays for determining the presence and concentration of protein antigens in a liquid sample.

2. Description of the Prior Art

In recent years, numerous immunoassay techniques have been developed to simplify operating procedures of existing methods and to provide new methods of improved speed, sensitivity and accuracy. In particular, solid-phase reactions have been especially valuable in making possible procedures that could not be performed with conventional homogenous phase reactions.

A solid-phase reaction is generally carried out between one reactant, the fixed component, immobilized on the surface of an insoluble support matrix, and a second reactant, the mobile component, in solution. Typically the reactants are immunological counterparts, which may be alternately disposed as either the fixed or the mobile component. As used herein, the term "immunological counterpart" denotes either an antigen or an antibody which reacts specifically with the corresponding antibody or antigen.

The reaction may be a conventional chemical reaction, a binding of the mobile component by the fixed component as in an immunochemical reaction between an antigen and an antibody, or it may be a binding of the mobile component by the fixed component accompanied by chemical transformation of one of the components such as occurs in an enzyme-catalyzed reaction. Quantitative results are obtained by measuring the formation of products or disappearance of reactants as in the case of conventional and enzyme-catalyzed reactions, and in measuring the amount of the mobile component bound or the amount of mobile component unbound, in the case of an immunochemical reaction.

Where the reaction consists of binding, in the absence of chemical change, techniques developed in the field of immunochemistry may be used to measure the extent of the reaction. Solid-phase reactions are especially suited for immunochemical assays because the reactants in bound form may readily be removed from the solution by virtue of their attachment to the solid phase. A variety of solid-phase supports have been developed and used in the prior art.

In solid-phase technology, the reagent or reagents used in the procedure are usually immobilized by being coated or bonded, either covalently or by adsorption to the solid-phase material, which is then immersed in the sample to be tested.

Examples of commonly used solid-phase materials include, but are not limited to, glass or polymeric tubes which are coated with the reagent or reagents on their internal surfaces; coated polymeric inserts; coated polymeric sticks; micro and macro beads formed by polymers and of glass; porous matrices; coated membranes; and tablets.

The earliest solid-phase systems were test tubes coated on the inside surface. Various improvements on these coated tubes resulted in tubes having a convoluted surface to increase surface area. Additionally, tubes were provided with detachable lower sections which may be both coated to achieve greater uniformity from tube to tube. This batch immobilization results in the outsides as well as the insides of the tubes being coated, and thereby wastes valuable immunological reagents.

The following U.S. Patents are noted to be representative of the prior art: U.S. Pat. No. 4,378,344, to Zahradnik et al.; U.S. Pat. No. 4,147,752, to Souvaniemie et al; U.S. Pat. No. 4,210,418, to Brown et al; U.S. Pat. No. 4,180,383, to Johnson; U.S. Pat. No. 4,170,454 to Meriadec et al; U.S. Pat. No. 4,280,816, to Elahi; U.S. Pat. No. 4,225,784 to Barrett; U.S. Pat. No. 3,826,619 to Bratu, Jr. et al; U.S. Pat. No. 3,793,445 to Updike et al.; U.S. Pat. No. 4,066,512 to Lai; and, U.S. Pat. No. 3,951,748 to Devlin.

Currently, solid-phase assays utilize the physical absorption of the substance to be assayed (typically, an antibody) out of solution onto the inside surface of plastic test tubes. Frequently, the surface is treated or pre-treated with a bifunctional coupling agent (such as glutaraldehyde) to improve the capacity and retention of the substance being assayed.

This type of immunoassay is subject to a number of disadvantages. For instance, only a certain type of plastic test tube will work and there is a binding variation since the plastic composition and molding characteristics of the test tube affect the binding ability of the substance being assayed. In the case where antibodies are the substance being assayed, there are the additional problems that physical absorption sometimes destroys the function of a percentage of antibody and/or may cause antibody leaching.

In addition, the tubes may not be stable for an extended period of storage, and are, in fact, frequently post-coated with a carrier protein such as bovine serum albumin or soluble gelatin for a hydrophilic protecting layer to enhance shelf-life. Generally, such tubes have a finite binding capacity (usually only about 1 $\mu$g of antibody can be absorbed to 1 $cm^2$ the inside surface of a plastic test tube) which limits the use of this technology to high titer antisera. Finally, the manufacture of such tubes in a consistent process requires costly equipment and much labor.

Various types of solid-phase matrices designed to be inserted into the reaction fluid have been disclosed in the prior art. These include sponge matrices, microporous membranes, closely-fitting inserts which squeeze the reactions fluid into a thin layer, disc shaped inserts, micro glass beads, coated macro beads and inserts having a plurality of water-insoluble fins. Many of these devices are illustrated in the U.S. Patents listed above, and to such extent, the disclosures of such patents are incorporated herein by reference.

All of the types of coated tubes and inserts suffer from two major disadvantages—excessive cost of manufacture and inconsistency between batches due to the multiple steps of manufacture. A need therefore exists for the development of a solid-phase support that may be uniformly, inexpensively and reliably manufactured and used.

SUMMARY OF THE INVENTION

In accordance with the present invention, a solid-phase support is prepared which is useful for like immunoassay procedures. The support is sized to fit into a test tube or like receptacle and may sit at the bottom thereof.

The support comprises a test tube liner having one closed end that is preferably rounded in shape. The liner has applied to its surfaces a coupling solution comprising a fixative to render the liner water-insoluble, a bioactive protein, and a bifunctional coupling agent to bind the bioactive protein to the liner surfaces. Test tube liners may be prepared from proteinaceous polymeric materials, polysaccharides, polyesters and polyamides, with the first-named class of materials being preferred. Fixatives may be selected from alkali metal and alkaline earth metal sulfates, bicarbonates and chlorides; lower alkanols, certain polyols such as polyethylene glycol, and mixtures of these. Bifunctional coupling agents may include certain aldehydes, such as $\alpha,\beta$-unsaturated aldehydes, dialdehydes, and mixtures.

The present invention also includes a method for the preparation of the solid-phase support which comprises providing the above-described test tube liner; contacting the liner with a sufficient quantity of the above-described coupling solution to render the liner water-insoluble, and to covalently bond to the surfaces of the liner the desired bioactive material; and thereafter separating the treated liner from the coupling solution, whereupon it may be dried for storage or prior to immediate use.

More particularly, the solid-phase immunoassay supports of the present invention may be produced by the treatment of a preformed soft gelatin capsule half with a coupling solution comprising a fixative, which may be an alkali metal salt, a bifunctional coupling agent and a bioactive protein which selectively reacts with the substance which is the subject of the immunoassay; processes for their production; and methods of use therefor.

Accordingly, it is a principal object of the present invention to provide supports for solid-phase immunoassays which can be easily and quickly inserted into test tubes for immunoassays.

It is a further object of the invention to provide supports for solid-phase immunoassays which have a precise quantity of bioactive protein coupled thereto.

It is a still further object of the invention to provide supports for solid-phase immunoassays which have a high binding capacity for the substance which is the subject of the immunoassay.

It is another object of the invention to provide supports for solid-phase immunoassay which have a built-in enhanced shelf life.

It is still another object of the invention to provide supports for solid-phase immunoassays which reduce or eliminate loss of the substance being assayed due to leaching or desorption.

It is an additional object of the invention to provide supports for solid-phase immunoassays which can be inexpensively and easily manufactured with a high degree of reproduceability.

These and other objects and advantages of the present invention will become more apparent from the following more detailed description thereof.

DETAILED DESCRIPTION OF THE INVENTION

In its broad aspect, the present invention is directed to a solid-phase immunoassay support, the processes for its preparation and methods of use thereof.

The solid-phase immunoassay support comprises a test tube liner having one closed, rounded end, and having applied to its surfaces a coupling solution, the coupling solution comprising a fixative to render the liner water-insoluble, a bifunctional coupling agent that attachs or binds to the surfaces of the test tube liner, and a bioactive protein that in turn also binds to the test tube liner via the coupling agent.

The invention also relates to a method for the preparation of the solid-phase immunoassay support. The method comprises in its broadest aspect, contacting the surfaces of the test tube liner with a coupling agent such as described above, to permit the fixative to render the liner water-insoluble, and to enable the bifunctional coupling agent to attach to the liner and to the bioactive protein so that the latter is thereby securely bound. The thus treated liner is then withdrawn or separated from the coupling solution, and dried or otherwise processed prior to either immediate use or packaging and storage.

The test tube liner may be prepared from a variety of film forming materials, among them proteinaceous polymers, polysaccharides, polyesters and polyamides. In particular, proteinaceous materials may comprise gelatin, collodion and collagen; polysaccharides include cellulose, its ethers and esters; polyesters may include polyethylene terephthalate; and polyamides comprise polyacrylamide. Preferred film forming materials comprise the proteinaceous polymers, and among them, gelatin in particular.

In a specific embodiment, the solid-phase immunoassay support of the present invention is conveniently prepared by treatment of a preformed soft gelatin capsule half with a coupling solution comprising an alkali metal salt fixative in sufficient quantity to render insoluble the gelatin capsule half, a bifunctional coupling agent, and a bioactive protein which selectively reacts with the substance which is the subject of the immunoassay.

The soft gelatin capsule half utilized in the present invention is a convenient and inexpensive article of commerce which contributes greatly to the overall economy of the invention. Although the capsules are available in a multitude of sizes, the size selected is generally one which will fit comfortably into the test tube in which the immunoassay is performed. For instance, gelatin capsules of the 000 size fit snugly but conveniently into the 12×75 mm test tube typically utilized for radioimmunoassay procedures.

As the gelatin capsules like most of the preferred film-forming materials, are completely water soluble, it is necessary to render them partially insoluble or "fix" them by contacting them with a high concentration of a fixative.

Suitable fixatives may be selected from a fairly broad group of materials, such as, for example, the alkali metal and alkaline earth metal salts formed with one or more substituents selected from the group consisting of chloride, bicarbonate and sulfate. Also certain other compounds, such as the lower alkanols, methanol and ethanol, and polyols such as polyethylene glycol may operate as solvent-type fixatives, all serving to render the film-forming material water-insoluble. Of the above, the alkali metal salts of the chlorides, sulfates and bicarbonates are preferred, and the sodium and potassium salts in particular. Sodium sulfate is typically utilized due to its economy and acceptability of use in diagnostic procedures.

A high concentration of the fixative, typically 30–80% saturation is necessary to achieve fixation of film-forming materials such as the gelatin capsules.

Although fixation can be achieved in a separate step prior to reaction of the gelatin capsule half with the bifunctional coupling agent, it is unnecessary to conduct separate steps. In fact, one of the features of the present invention is that fixation may be conducted concurrently with the coupling of the bioactive protein to the test tube liner.

One of the characteristics of a properly prepared solid-phase assay support bearing a bioactive protein thereon, is that the support or substrate must be relatively insoluble, while the bioactive material must be and remain soluble. Any alteration in this dichotomy will result in defects in the support, and corresponding inaccuracies on inoperability of the support in immunoassay procedures.

One of the obstacles faced by those in the art and the inventor herein as well, was the deleterious side effects that certain fixatives had on the activity and presence of the bioactive protein in the finally prepared support. Thus, when ammonium sulfate was employed as the fixative, it was found to react with the bifunctional coupling agent, and thereby prevented the latter from forming the desired releasable connection between the substrate and the bioactive material. It was thus generally accepted, that as negative interaction between the fixative and the coupling agent could occur, the two would be applied to the substrate separately and consecutively.

By contrast and in destinction of the foregoing, it has been found possible to practice the method utilizing a coupling solution containing both the fixative and the bifunctional coupling agent, which is correspondingly concurrently applied to the surface of the test tube liner. The operability of the present method and the coupling solution is believed to be attributable in part to the particular fixatives and bifunctional coupling agents employed, as well as to the other characteristics of the coupling solution, such as pH and the concentrations of the respective components.

For example, the coupling solution is preferably prepared with a pH near neutrality, as this pH value has been found to optimize the level of binding and the consequent level of activity of the bioactive protein to the substrate or liner. Also, the relation between the pH of the solution and the concentration of the bifunctional coupling agent, (e.g. glutaraldehyde), appears to affect the ability of the test tube liner (gelatin capsule) to retain its shape. Thus, illustrative optimal concentrations of ingredients and pH values have been identified: (a) a solution having a pH of 7, a glutaraldehyde concentration of 0.5% and a 50% saturated solution of sodium sulfate; and (b) a solution with a pH of 10.5, a glutaraldehyde concentration of 0.125% and a 50% saturated solution of sodium sulfate.

As a general observation, the foregoing parameters may be adjusted to suit the preparation of particular supports for specific assay procedures, and the conditions expressed above are illustrative, only. To the extent that it is desirable to achieve an optimal combination of bioactive protein binding and activity, and capsule shape retention, the conditions wherein the pH approaches neutrality and a higher concentration of the bifunctional coupling agent, such as illustrated in scenario (a) above, is preferred.

Most conveniently therefore, the fixation is achieved simply by the addition of the fixative, the bifunctional coupling agent and the bioactive protein at the same time to the test tube liner. The coupling reaction between the bifunctional coupling agent and the liner itself also aids in the insolubilization (or "fixing") of the liner in the instance where the liner is a gelatin capsule half, as a net of crosslinks form between adjacent strands of protein in the gelatin of the capsule.

While the concentration of the coupling agent affects the binding capability of the capsule surface, this is not so in the case of the fixative. Thus, variations in fixative concentration of from 10% to 50% of the coupling solution were found to have no effect upon the binding capability of the capsule surface.

The bifunctional coupling agent utilized in the present invention may be any of the agents well known in the art for such purposes. Typical coupling agents include the aldehyde coupling agents such as the $\alpha,\beta$-unsaturated aldehydes, dialdehydes and mixtures thereof. The $\alpha,\beta$-unsaturated aldehydes are represented by the formula

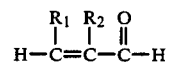

wherein $R_1$ and $R_2$ can independently be hydrogen or a methyl group. Representative of this type of aldehyde are acrolein, methacrolein and 2-butenal. Dialdehydes typically utilized include glutaraldehyde, propanedial and butanedial. For the purposes of this invention, glutaraldehyde is a preferred bifunctional coupling agent.

In the instance where the test tube liner is prepared from gelatin and one of these aldehydes is contacted with the surface of the gelatin, the gelatin is stabilized and polymerized by cross-linking, and aldehyde active moieties are fixed to the surfaces. These moieties are believed to be carbonyl groups and as such are highly reactive to the amine groups of bioactive proteins, since they form covalent bonds between the protein particles and the biologically active substances.

Other bifunctional coupling agents which can be utilized are compounds having two or more of the following reactive groups: azo, sulfonic acid, fluoro groups activated by nitro groups, azide, imine and reactive chloro groups connected to a ring having proper resonance structure. These reactive groups are capable of reacting with the primary amino, sulfylhydryl, carboxylic, hydroxyl and phenolic groups in the substances that constitute the majority of the materials disclosed herein as suitable for the preparation of the test tube liner, gelatin being illustrative therof, as well as the bioactive protein to be coupled thereto. Representative of such other coupling agents are bis-diazobenzidine, disulfonic acid, tetraazo-p-phenylenediamine, difluorodinitrobenzene, difluorodinitrophenylsulfone, a carbodiimide, toluene diisocyanate, cyanuric chloride and dichlorotriazine. Carbodiimides which can be employed are N,N-dicyclohexylcarbodiimide, 1-ethyl-3(3-dimethyl aminopropyl)carbodiimide hydrochloride and 1-cyclohexyl-3-(2-morpholinyl-(4)-ethylcarbodiimide)-methyl-p-toluene sulfonate.

The amount of bifunctional coupling agent utilized in the process of this invention will depend upon the particular bioactive protein to be coupled to the test tube liner and on the pH of the coupling solution, as discussed earlier herein. The amount can be readily determined by those skilled in the art but typically will be an amount sufficient to cross-link the liner and provide sufficient sites for coupling to the liner for carrying out the desired immunoassay procedure. In the case where the liner is a gelatin capsule half and the coupling agent is an aldehyde such as glutaraldehyde, this is generally an amount from 0.1 to about 10% (w/v), preferably about 1.25 to about 2% (w/v).

A wide range of bioactive proteins can be attached to the test tube liner in accordance with this invention. Such substances include antigens, antibodies and enzymes. Typical antibodies which may be attached to the test tube liner include those against the haptens digoxin, triiodothyronine (T3), thyroxine (T4), TSH, angiotensin and insulin; the various biologically active steroids; the bile acids; other polypeptide hormones; enzymes and isoenzymes; and pharmacologically active substances such as drugs of abuse as well as those used for therapy and others.

Enzymes which may be attached to the test tube liner include diastase, glucose oxidase, urease, maltase, amylase, peroxidase, and other enzymes and coenzymes.

Depending upon the particular type of assay, the bioactive protein can be varied. For instance, for radioimmunoassays (RIA), an antibody specific for an analyte is coupled to the test tube liner. Enzyme immunoassays, fluorescence immunoassays, chemiluminescent immunoassays, and immunoradiometric assays would utilize differently tagged analytes or antibodies with the test tube liners.

The amount of bioactive protein utilized in the practice of this invention will depend on the particular bioactive protein. Such amounts can readily be determined by those skilled in the art. Typically, it will be an amount sufficient to carry out the determination or procedure of the immunoassay being conducted. Since in the instance of gelatin capsule halves, the test tube liner has a high level of binding sites, the amount of bioactive protein which can be bound thereto is high, resulting in a support which has a high binding capacity and which can therefore be utilized for lower titer antisera.

The process of the present invention is carried out in aqueous media under conditions which will not denature the bioactive protein. Typical conditions include temperatures of 4°–50° C. and pH ranges of from about 3 to about 10. Preferably, room temperature and a pH around 7 are utilized. In batch procedures, the test tube liners are added to a container holding a solution of the salt fixative, coupling agent and bioactive protein. After the reaction is completed, the liners are washed several times with buffer to remove residual and unreacted material. This batchwise procedure is fast and easily accomplishes the production of consistently coated test tube inserts.

Alternatively, the liners can be inserted into test tubes and then reacted with the solution containing the fixative, coupling agent and bioactive protein. This procedure can be utilized with automated equipment of the type now used for coating plastic tubes. After the reaction is complete, the tubes are decanted emptying their contents and then washed successively to remove excess unreacted reagent. The support thus formed is shelf-stable without the necessity of additional coatings or preservatives.

The present invention also encompasses the method of using the support prepared by the above process for immunoassays to determine the presence and concentration of an analyte in a liquid medium, and comprises adding to a test tube or similar container containing said support the analyte-containing fluid so as to allow the analyte to react with its immunological counterpart, and analyzing by the appropriate method the reacted analyte. Depending upon the exact type of immunoassay being performed, the analysis will, of course, vary. For instance, in the case of a radioimmunoassay (RIA), an antibody specific for an analyte is bound to the test tube liner and the analyte concentration is determined by measuring the level of competition it has for it in the presence of a sample containing it.

Alternatively, the test tube liner halves can be reacted with the fixative (to render it insoluble) and the bifunctional coupling agent only. Then, the liner would be contacted with the analyte-containing fluid, for instance a radiologically tagged analyte-containing fluid, to covalently bind the analyte to the support. This method allows a direct assay of the analyte without the necessity of the coupling of the bioactive protein to the test tube liner.

The following examples describe in detail the preparation of the supports of the present invention and methods of use therefor. It will be apparent to those skilled in the art that many modifications, both of materials and methods, may be practiced without departing from the purpose and intent of this disclosure.

EXAMPLE I

A solid-phase immunoassay support is produced by the following procedure:

Ten large gelatin capsule halves or thirteen small halves from a gelatin capsule size 000 are added to a beaker containing 50 ml. of "coupling solution". This solution consists of sodium sulfate, between 30–80% of saturation, 0.25% glutaraldehyde and diluted bioactive protein such as alkaline phosphatase-labeled goat IgG-(IgG-ALP). The actual dilution of bioactive protein is determined by experiment depending upon the level of activity desired. The capsule halves are stirred in this solution at room temperature for 1–18 hours. After this treatment, the reacted insoluble capsule halves are washed with three changes of 200 ml phosphate buffered saline (pH 7).

The capsule halves are then air-dried by placing them open end down on a flat surface.

EXAMPLE II

The procedure of Example I is repeated except that in place of air-drying, the wet capsules are treated with 50% glycerol solution so that they remain moist. They are then placed directly inside 12×75 mm test tubes for future use.

EXAMPLE III

Further supports were prepared in accordance with the procedures of the present invention. Accordingly, three short gelatin capsule halves, type 000, are added to 20 ml of coupling solution containing 50% saturated sodium sufate, 0.5% glutaraldehyde and 27.5, 55, 87, 110, and 220 ng/ml of alkaline phosphatase-labeled goat IgG (IgG-ALP). The capsule halves are stirred in this solution for two hours at room temperature. Then the reacted insoluble capsules are washed with three changes of 50 ml of 50 mM Tris-saline, pH 7. They are then placed inside 12×75 mm test tubes. One ml of substrate solution for the enzyme, 10 mM p-nitrophenyl phosphate in 0.1M 1-amino-2-methyl propandiol, pH 10.5 with 1 mM $MgCl_2$ is added to these tubes and incubated for 30 minutes at room temperature. One ml of 1M NaOH is then added to stop the color generating reaction. The contents are then read spectrophotometrically at 410 nm. The results are set forth in Table I, below.

TABLE I

| ng/ml IgG-ALP in coupling solution | μl of Dilution Bound |
| --- | --- |
| 27.5 | 45 |
| 55 | 58 |
| 87.5 | 55 |
| 110 | 55 |
| 220 | 52 |

The above results confirm that the preparation of solid-phase supports in accordance with the invention is operable and further that the activity of the supported antibody can be easily controlled. More particularly, goat IgG-ALP was bound and retained its activity under the conditions of the invention, and the amount of such activity was determined to be linearly related to the concentration of the labeled autibody in the coupling solution.

EXAMPLE IV

In this series of tests, it was sought to determine the retention and reactivity of unlabeled antibody after coupled to a solid-phase support in accordance with the invention. Accordingly, a series of gelatin capsule halves were prepared in the same manner as set forth in EXAMPLE III, with the exception that the antibody used was anti-human chorionic gonadotrophin (anti-hCG). Sample supports were prepared with anti-hCG concentrations of 1, 2.5, 5 and 10 μg/ml. The antibody-coated capsules were allowed to react in a test tube with 75 mIU/ml of hCG-ALP in 0.05M Tris saline (pH 7) containing 0.1% Bovine serum albumin, for from 1 to 24 hours. Enzyme activity was determined as described above in EXAMPLE III, and the results are set forth in Table II, below.

TABLE II

| μg of Anti-hCG/ml in Coupling Solution | HOURS INCUBATION | | | |
| --- | --- | --- | --- | --- |
|  | 1 | 2 | 4 | 24* |
| 0 (NSB) | 0 | 0.01 | 0.02 | 0.01 |
| 1 | 0 | 0 | 0.01 | 0.01 |
| 1 | 0.06 | 0.1 | 0.2 | 0.25 |
|  | 0.07 | 0.11 | 0.2 | 0.26 |
| 2.5 | 0.10 | 0.19 | 0.36 | 0.52 |
|  | 0.10 | 0.18 | 0.36 | 0.45 |
| 5.0 | 0.15 | 0.26 | 0.43 | 0.67 |
|  | 0.13 | 0.26 | 0.44 | 0.72 |
| 10.0 | 0.16 | 0.29 | 0.52 | 0.85 |
|  | 0.17 | 0.30 | 0.53 | 0.82 |

*At this time interval, it is found that equilibrium conditions are approximated.

The above results demonstrate that the unlabeled antibody anti-hCG was covalently bound to the capsules, and that as observed earlier the levels of the antibody were linearly related to the concentration of the antibody in the coupling solution. In addition, the closeness of the replicate values shows that the binding of the antibody to the capsules takes place in a reproducible, uniform manner.

EXAMPLE V

This experiment was also performed as described in EXAMPLE III for the purpose of comparing the binding characteristics of labeled antibody to gelatin capsules, polyethylene tubes, and polystyrene tubes, the latter tubes representing the prior art. For each dilution of alkaline phosphatase-labeled IgG, 1 ml of thereof was placed into each of three 12×75 mm untreated gelatin, polyethylene and polystyrene test tubes, and incubated for 2 hours. After this, the solution was decanted from the tubes and washed with three successive changes of Tris-saline buffer containing 0.05% Tween 20. All of the test tubes were then assayed for retained enzyme activity, and the results of these assays are set forth in Table III, below.

TABLE III

| ng/ml in Coupling Solution | GELATIN CAPSULE μl of Dilution Coupled | POLYSTRENE μl of Dilution Coupled | POLYETHYLENE μl of Dilution Coupled |
| --- | --- | --- | --- |
| 27.5 | 45 | 24 | 80 |
| 55 | 58 | 33 | 37 |
| 87.5 | 55 | 32 | 35 |
| 110 | 55 | 33 | 33 |
| 220 | 52 | 30 | 33 |

These data support the conclusion that under the given conditions, the gelatin capsules bind more IgG-ALP conjugate than either of the plastic tubes. The comparative data thus demonstrates the improved performance of the supports prepared in accordance with the present invention.

It is understood that the invention is not limited to the illustrations described and shown herein, which are deemed to be merely illustrative of the best modes of carrying out the invention, and which are suitable of modification of form, size arrangement of parts and details of operation. The invention rather is intended to encompass all such modifications which are within the spirit and scope and defined by the claims.

What is claimed is:

1. A method for the preparation of a solid-phase immunoassay support which comprises:

A. providing a preformed test tube liner defining a rounded, closed end and prepared from a film forming material selected from the group consisting of proteinaceous polymeric materials, polysaccharides, polyesters and polyamides, B. contacting said test tube liner with a sufficient quantity of a coupling solution to render said test tube liner water-insoluble, said coupling solution comprising, a fixative selected from the group consisting of alkali metal, alkaline earth metal sulfates, bicarbonates, chlorides; lower alkanols, polyols, and mixtures thereof, a bifunctional coupling agent, and a bioactive protein for participation as a reactant in said solid phase immunoassay, said biofunctional coupling agent being capable of bonding to said liner said bioactive protein.

2. The method of claim 1 wherein said bifunctional coupling agent comprises a compound having one or more functional groups selected from the group consisting of aldehydes, azo groups, sulfonic acid groups, fluoro groups activated by nitro groups, azides, imines, and reactive chloro groups connected to a ring having a resonance structure.

3. The method of claim 2 wherein said bifunctional coupling agent has one or more aldehyde groups and is selected from the group consisting of α,β-unsaturated aldehydes, dialdehydes and mixtures thereof.

4. The method of claim 1 wherein said fixative comprises the alkali metal salts of a member selected from the group consisting of chlorides, bicarbonates, sulfates and mixtures thereof.

5. The method of claim 4 wherein said alkali metal is selected from the group consisting of sodium, potassium and mixtures thereof.

6. The method of claim 1, said method comprising:
  A. contacting half of a preformed soft gelatin capsule with a coupling solution comprising,
    an alkali metal salt of a member selected from the group consisting of chlorides, bicarbonates, sulfates, and mixtures thereof, to serve as a fixative, and present in an amount sufficient to render the gelatin half capsule water-insoluble,
    a bifunctional coupling agent, and
    a bioactive protein which selectively reacts with the substance which is the subject of the immunoassay; and
  B. separating the reacted insoluble gelatin capsule half from the coupling solution.

7. A process according to claim 6 wherein the bifunctional coupling agent is present in an amount of from 0.1% to 2% w/v.

8. A process according to claim 6 wherein the size of the preformed soft gelatin capsule half is selected so as to fit a 12×75 mm test tube.

9. A process according to claim 6 wherein the bifunctional coupling agent is glutaraldehyde.

10. A process according to claim 6 wherein the bioactive protein is an antigen.

11. A solid-phase support for immunoassay which support is sized to fit a test tube, said support comprising a test tube liner having one closed, rounded end, said liner having applied to the surfaces thereof a coupling solution comprising a fixative to render said liner water-insoluble, a bifunctional coupling agent, and a bioactive protein covalently bound by said bifunctional coupling agent to the surfaces of said liner.

12. The support of claim 11 wherein said test tube liner is prepared from a material selected from the group consisting of proteinaceous polymeric materials, polysaccharides, polyesters and polyamides.

13. The support of claim 11 wherein said test tube liner is prepared from a material selected the group consisting of gelatin, collodion, collagen, cellulose, cellulose ethers, cellulose esters, agarose, and polyacrylamides.

14. The support of claim 11 wherein said fixative is selected from the group consisting of alkali metal and alkaline earth metal sulfates, bicarbonates, chlorides and mixtures thereof; lower alkanols; polyols; and mixtures thereof.

15. The support of claim 11 wherein said bifunctional coupling agent comprises a compound having one or more functional groups selected from the group consisting of aldehyes, azo groups, sulfonic acid groups, fluoro groups activated by nitro groups, azides, imines, and reactive chloro groups connected to a ring having a resonance structure.

16. The support of claim 11 wherein said bifunctional coupling agent has one or more aldehyde groups and is selected from the group consisting of $\alpha,\beta$-unsaturated aldehydes, dialdehydes and mixtures thereof.

17. The support of claim 11 wherein said support comprises a soft gelatin capsule half fixed with an alkali metal salt solution to render it insoluble, said capsule having a bioactive protein covalently bound thereto by means of a bifunctional coupling agent.

18. A support according to claim 17 wherein the gelatin capsule half is sized so as to fit a 12×75 mm test tube.

19. A support according to claim 17 wherein the bioactive protein is covalently bound to the gelatin capsule half by glutaraldehyde.

20. In a method for determining the presence and concentration of an analyte in a liquid medium by immunoassay wherein a supported immunological counterpart to said analyte is brought into contact with said analyte, the improvement which comprises utilizing a solid-phase support for immunoassay which support is sized to fit a test tube, said support comprising a test tube liner having one closed, rounded end, said liner having applied to the surfaces thereof a coupling solution comprising a fixative to render said liner water-insoluble, a bifunctional coupling agent, and a bioactive protein covalently bound by said bifunctional coupling agent to the surfaces of said liner.

21. A method of determining the presence and concentration of an analyte in a liquid medium by immunoassay which comprises adding to a test tube or similar container containing a solid-phase support for immunoassay which support is sized to fit a test tube, said support comprising a test tube liner having one closed rounded end, said liner having applied to the surfaces thereof a coupling solution comprising a fixative to render said liner water-insoluble, a bifunctional coupling agent, and a bioactive protein covalently bound by said bifunctional coupling agent to the surfaces of said liner, the analyte containing fluid so as to allow the analyte to react with its immunological counterpart, and analyzing by the appropriate method the reacted analyte.

* * * * *